(12) United States Patent
Löfholm et al.

(10) Patent No.: US 11,330,925 B2
(45) Date of Patent: May 17, 2022

(54) APPARATUS FOR FACILITATING DONNING A GARMENT

(71) Applicant: GloveMe Scandinavia AB, Nyköping (SE)

(72) Inventors: Håkan Johan Löfholm, Huddinge (SE); Taisto Kalevi Nyström, Nyköping (SE); Patrik Härnman, Linköping (SE)

(73) Assignee: GloveMe Scandinavia AB, Nyköping (SE)

( * ) Notice: Subject to any disclaimer, the term of this patent is extended or adjusted under 35 U.S.C. 154(b) by 57 days.

(21) Appl. No.: 17/053,159

(22) PCT Filed: May 16, 2019

(86) PCT No.: PCT/SE2019/050445
§ 371 (c)(1),
(2) Date: Nov. 5, 2020

(87) PCT Pub. No.: WO2019/231377
PCT Pub. Date: Dec. 5, 2019

(65) Prior Publication Data
US 2021/0161321 A1    Jun. 3, 2021

(30) Foreign Application Priority Data

May 31, 2018 (SE) .................................. 1850657-6

(51) Int. Cl.
*A47G 25/90* (2006.01)
(52) U.S. Cl.
CPC .................................. *A47G 25/904* (2013.01)

(58) Field of Classification Search
CPC .... A47G 25/90; A47G 25/904; A47G 25/905;
A61B 42/40; A61B 42/50
See application file for complete search history.

(56) References Cited

U.S. PATENT DOCUMENTS 6,932,253 B2 *   8/2005   Sato ...................... A47G 25/904
223/111
2005/0155133 A1   7/2005   Sato
(Continued)

FOREIGN PATENT DOCUMENTS

DE    102004025299 A1 *  12/2005
WO    WO 0249526 A1 *   6/2002
(Continued)

*Primary Examiner* — Ismael Izaguirre
(74) *Attorney, Agent, or Firm* — Blank Rome LLP

(57) ABSTRACT

The present invention relates to an apparatus (800) arranged for facilitating donning a garment (52) comprising a cuff on a part of a human body. The apparatus (800) comprises a at least one cuff opening arrangement (600, 700) arranged to open a cuff of a garment (52). The at least one cuff opening arrangement (600, 700) comprises a first (100) and a second (200) cuff opening assembly, each comprising a first (110, 210) and a second (120, 220) arm which are arranged to rotate around a first (GA1) and a second (GA2) geometrical axis, respectively. When the first (110, 210) and second (120, 220) arms are inserted into a cuff of the garment (52) and rotated around the first (GA1) and second (GA2) geometrical axes, respectively, the first (110, 210) and second (120, 220) arms are separated such that the cuff of the garment (52) is expanded. Thereby, facilitating donning the garment (52) on a part of a human body.

15 Claims, 9 Drawing Sheets

(56) References Cited

U.S. PATENT DOCUMENTS

2007/0170213 A1\* 7/2007 Gaines .................. A61B 42/40
  223/111
2017/0156531 A1 6/2017 Barker et al.
2017/0273750 A1\* 9/2017 Gaines .................. A61B 42/40

FOREIGN PATENT DOCUMENTS

| WO | WO 2005/013842 A2 | 2/2005 |
| WO | WO 2016046337 A1 \* | 3/2016 |
| WO | WO 2016/174672 A1 | 11/2016 |
| WO | WO 2017/106680 A2 | 6/2017 |

\* cited by examiner

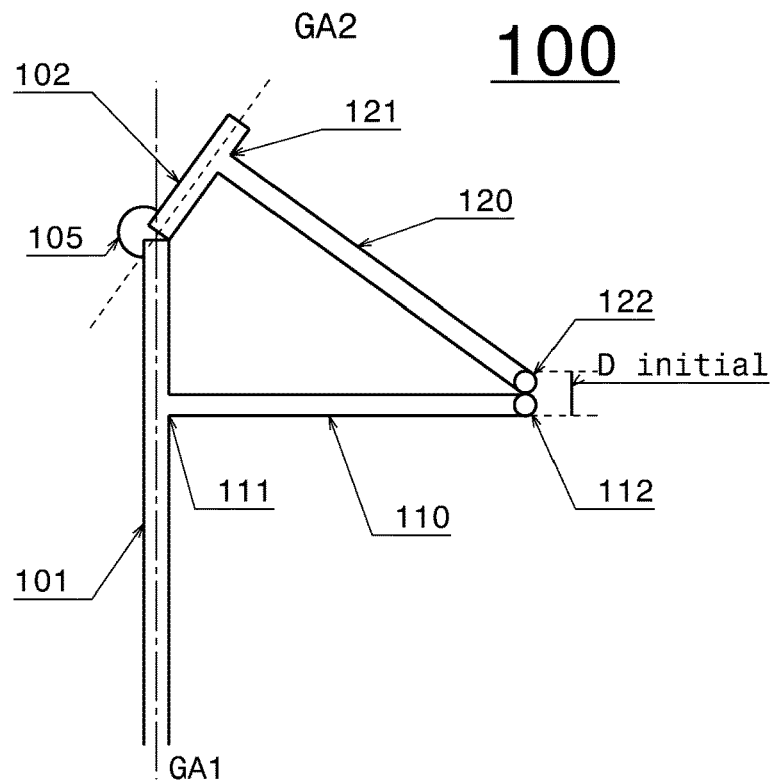
Fig. 3c
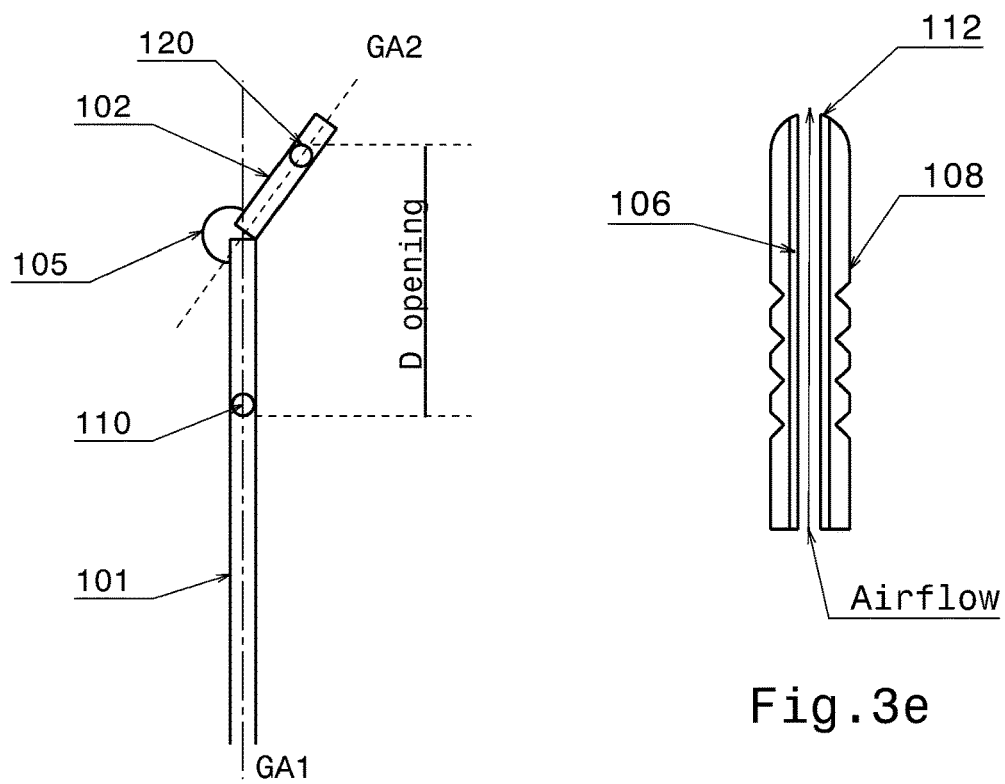
Fig. 3d
Fig. 3e

APPARATUS FOR FACILITATING DONNING A GARMENT

TECHNICAL FIELD

The present invention relates to an apparatus arranged for facilitating donning a garment comprising a cuff on a part of a human body.

BACKGROUND

In this document, the embodiments of the present invention are often described in relation to gloves, such as disposable and/or sterile gloves. However, the present invention is not limited to usage in connection with gloves. Instead, the present invention may be generally utilized for donning essentially any type of garment on essentially any body part.

Disposable gloves are today used by employees in a number of different areas, such as e.g. in the health care sector and the food industry. Disposable gloves are typically worn to protect the hands of the user and/or to prevent spreading of bacteria and other agents. Due to stricter hygienic requirements and safety aspects, the use of disposable gloves is increasing and is likely to continue to increase in the future.

SUMMARY

One disadvantage with using disposable gloves is that it may be difficult and time consuming to put them on, especially if the gloves are tight and/or the hands are damp. In addition, the risk of damaging a glove when it is being put on is high. These drawbacks may not be that severe for persons which only occasionally uses disposable gloves. However, a lot of persons working with disposable gloves need to regularly change gloves. For example, a nurse typically puts on a new pair of gloves for each new patient, and a person working behind a deli counter puts on a new pair of gloves for each new customer. Hence, in certain professions, many glove changes are performed per day per employee. If each of these glove changes is time consuming, there are major time losses and thereby costs associated with the changing of disposable gloves.

The use of disposable gloves in environments with strict hygienic requirements poses additional challenges related to contamination. When disposable gloves are put on manually, the user typically needs to touch the outside of the disposable gloves. Although care is exercised, it may be difficult to avoid touching areas of the disposable glove which is later going to come in contact with e.g. a patient or food. Hence, there is a high risk that disposable gloves are contaminated as they are being put on.

To avoid the above described disadvantages related to applying and changing disposable gloves, machines which automatically apply gloves on the hands of a user have been developed. This type of machines is hereafter referred to as glove donning machines. Typically, a conventional glove donning machine uses vacuum or suction to inflate the glove and allow the hand to be inserted into the glove. One disadvantage with using vacuum or suction is the noise produced by the vacuum pump. In addition, it is difficult to control the suction power such that the glove can be opened properly. Other types of known glove donning machines rely on complex movement of mechanical parts and requires advance mechanical structures which may be prone to malfunction.

Consequently, there is a need for an improved glove donning machine.

An objective of embodiments of the present invention is to provide a solution which mitigates or solves the drawbacks and problems of prior art.

The above and further objectives are achieved by the subject matter of the independent claim. Further advantageous implementation forms of the present invention are defined by the dependent claims and other embodiments.

According to an aspect of the invention, the above mentioned and other objectives are achieved with an apparatus arranged for facilitating donning a garment comprising a cuff on a part of a human body; characterized by a garment fetching arrangement arranged for fetching a garment from a garment storage and placing the garment in a donning position;

at least one cuff opening arrangement arranged to open a cuff of the garment in the donning position, and comprising a first and a second cuff opening assembly, each of the first and second cuff opening assemblies comprising:

a first arm comprising a first proximal end and a first distal end, the first arm being rotatable around a first geometrical axis;

a second arm comprising a second proximal end and a second distal end, the second arm being rotatable around a second geometrical axis; wherein the first and second arms are arranged to rotate around the first and second geometrical axes, respectively, between an initial position and an opening position, and said first and second geometrical axes are arranged with an angle α to each other, said angle α being selected such that the first and second distal ends are at a first initial distance from each other in the initial position, and are separated to a first opening distance from each other in the opening position, when the first and second arms are rotated around the first and second geometrical axes, respectively, the first opening distance being greater than the first initial distance.

An advantage with the apparatus according to the aspect is that the first and the second cuff opening assemblies can expand a cuff of a garment using rotating arms, i.e. the first and second arms rotating around their first and second geometrical axes, respectively. Thereby, an automated expansion of the cuff of the garment can be achieved which is both simple and fast. The use of rotating arms further allows the apparatus to be made compact as the arms can be moved around their own axes.

A further advantage is that the first and second distal ends can be rotated and separated from each other in one movement. Thereby, a substantial expansion of the cuff of the glove can be achieved in a simple and fast way.

According to an embodiment of the invention, the first arm is arranged to rotate around a first shaft extending along the first geometrical axis; and the second arm is arranged to rotate around a second shaft extending along the geometrical axis.

An advantage with this embodiment is that the first and second shafts can be fixed in relation to each other with only the first and second arms rotating. Thereby, a simple construction is achieved.

According to an embodiment of the invention, the first arm is arranged to rotate together with a rotatable first shaft extending along the first geometrical axis and being rotatable around the first geometrical axis; and the second arm is arranged to rotate together with a rotatable second shaft extending along the second geometrical axis and being rotatable around the second geometrical axis.

An advantage with this embodiment is that the first and second arms can be integrated with the first and second shafts, respectively. Thereby, a flexible construction is achieved, allowing e.g. the arms and shafts to be hollow such that an air tube can be led through a shaft and further out through an arm.

According to an embodiment of the invention, the first and second distal ends are inserted into a cuff of a garment placed in the donning position when the first and second arms are rotated around the first and second geometrical axes, respectively, from the initial position to the opening position.

An advantage with this embodiment is that the cuff of the garment is expanded by the rotation of the arms inside the garment.

According to an embodiment of the invention, a first and a second distal end of the first and second arms of the first cuff opening assembly are at a second initial distance from a first and a second distal end of the first and second arms of the second cuff opening assembly, respectively, in the initial position;

the first and second distal ends of the first cuff opening assembly are at a second opening distance from the first and second distal ends of the second cuff opening assembly, respectively, in the opening position; and the second opening distance is greater than the second initial distance.

An advantage with this embodiment is that the first and second arms of the first and second cuff opening assemblies, respectively, are separated in two directions by the above mentioned rotational movement, which efficiently opens the cuff to facilitate donning.

According to an embodiment of the invention, the first and second distal ends of the first and second arms of the first cuff opening assembly and the first and second distal ends of the first and second arms of the second cuff opening assembly in the initial position defines an initial area; and the initial area is smaller than an area of an opening of the garment in its relaxed state.

An advantage with this embodiment is that the first and second arms of the first and second cuff opening assemblies, respectively, are close together in the initial position and can thereby easily be inserted into the opening/cuff of the garment.

According to an embodiment of the invention, the first and second distal ends of the first and second arms of the first cuff opening assembly and the first and second distal ends of the first and second arms of the second cuff opening assembly in the opening position defines an opening area; and the opening area is greater than an area of an opening of the garment in its relaxed state.

An advantage with this embodiment is that the first and second arms of the first and second cuff opening assemblies, respectively, are separated from each other in the opening position such that the cuff of the garment is expanded, whereby donning is facilitated.

According to an embodiment of the invention, the first arm comprises a first proximal part and a first distal part being resiliently connected to each other; and the second arm comprises a second proximal part and a second distal part being resiliently connected to each other.

An advantage with this embodiment is that the first and second arms are more flexible and can provide a large/substantial movement within a small space/cabinet of the apparatus, whereby a compact apparatus is provided.

According to an embodiment of the invention, at least one of the first proximal part and the first distal part and the second proximal part and the second distal part, respectively, are resiliently connected by means of one or more in the group of:

at least one spring joint; and a resilient material of at least one of the first and second arms.

According to an embodiment of the invention, in the initial position, the first and second distal parts of the first cuff opening assembly are in contact with the first and second distal parts of the second cuff opening assembly, respectively, such that the first distal part of the first cuff opening assembly are at a first initial angle to the first proximal part of the first cuff opening assembly;

the second distal part of the first cuff opening assembly are at a second initial angle to the second proximal part of the first cuff opening assembly;

the first distal part of the second cuff opening assembly are at a third initial angle to the first proximal part of the second cuff opening assembly;

the second distal part of the second cuff opening assembly are at a fourth initial angle to the second proximal part of the second cuff opening assembly.

An advantage with this embodiment is that the first and second distal parts of the first and second arms, respectively, can be arranged to allow the first and second arms to easily be inserted into the opening/cuff of the garment in the initial position.

According to an embodiment of the invention, in a subsequent position the first and second distal parts of the first and second cuff opening assemblies are in contact with an inside of the cuff of the garment, such that the first distal part of the first cuff opening assembly are at a first subsequent angle to the first proximal part of the first cuff opening assembly;

the second distal part of the first cuff opening assembly are at a second subsequent angle to the second proximal part of the first cuff opening assembly;

the first distal part of the second cuff opening assembly are at a third subsequent angle to the first proximal part of the second cuff opening assembly;

the second distal part of the second cuff opening assembly are at a fourth subsequent angle to the second proximal part of the second cuff opening assembly.

An advantage with this embodiment is that the angles between the first and second distal parts are affected by the force created when the cuff opening assemblies are in contact with the inside of the garment in the subsequent position.

According to an embodiment of the invention, the first subsequent angle is greater than a first initial angle;

the second subsequent angle is greater than a second initial angle;

the third subsequent angle is greater than a third initial angle;

the fourth subsequent angle is greater than a fourth initial angle.

An advantage with this embodiment is that the first and second arms are arranged to expand the garment in the subsequent position to facilitate donning.

According to an embodiment of the invention, when the subsequent position corresponds to the opening position, the first subsequent angle, the second subsequent angle, the third subsequent angle, and the fourth subsequent angle are approximately 180 degrees.

An advantage with this embodiment is that the first and second arms are providing a large/substantial expansion of the garment in the opening position. Furthermore, the first and second arms are straight, i.e. the angle is 180 degrees, in the opening position which, means that they are out of the way for a hand as the garment is donned on the hand of a user.

According to an embodiment of the invention, the first and second arms of the first and second cuff opening assemblies, respectively, are coupled with a first coupling means, such that the first and second arms rotates synchronously around the first and second geometrical axes, respectively.

An advantage with this embodiment is that a synchronized and smooth rotation of the first and second arms can be achieved.

According to an embodiment of the invention, at least one of the first and second arms of the first cuff opening assembly is coupled to at least one of the first and second arms of the second cuff opening assembly with a second coupling means, such that the first and second arms of the first and second cuff opening assemblies rotate synchronously around their respective geometrical axes; and the first and second arms of the first cuff opening assembly rotates in a first rotation direction and the first and second arms of the second cuff opening assembly rotates in a second rotation direction, the second rotation direction being opposite to the first rotation direction.

An advantage with this embodiment is that a synchronized and smooth rotation of the first and second arms of the first and second cuff opening assemblies, respectively, can be achieved.

According to an embodiment of the invention, the at least one cuff opening arrangement further comprises:

at least one rotation providing means coupled to at least one of the first and second arms of the first and second cuff opening assemblies, arranged to cause the rotation of at least one of the first and second arms of the first and second cuff opening assemblies between the initial position and the opening position.

According to an embodiment of the invention, the at least one rotation providing means includes:

at least one rod coupled to at least one of the first and second arms of the first and second cuff opening assemblies; wherein when the at least one rod is in a first position, the first and second arms of the first and second cuff opening assemblies are in the initial position; and when the at least one rod is in a second position, the first and second arms of the first and second cuff opening assemblies are in the opening position.

An advantage with this embodiment is that the rotational movement is provided by a mechanical rotation means, which is reliable and dependable.

According to an embodiment of the invention, the at least one rotation providing means comprises:

at least one displacement means coupled to the at least one rod and arranged to displace the at least one rod between the first and second positions.

According to an embodiment of the invention, the apparatus further includes a first cuff opening arrangement and a second cuff opening arrangement; wherein at least one rod of the first cuff opening arrangement is coupled to a at least one rod of the second cuff opening arrangement;

the at least one rotation providing means comprises:

a displacement means coupled to one or more of the at least one rod of the first or second cuff opening arrangements and arranged to displace the at least one rod of the first and second cuff opening arrangements, respectively, between the first and second positions.

An advantage with this embodiment is that a synchronized rotation of the first and second arms of the first and second cuff opening arrangements, respectively, can be achieved.

According to an embodiment of the invention, the at least one rotation providing means comprises:

at least one rotary engine coupled to at least one of the first and second arms of the first and second cuff opening assemblies; wherein the at least one rotary engine is arranged to rotate the first and second arms of the first and second cuff opening assemblies from the initial position to the opening position.

An advantage with this embodiment is that the rotational movement is provided with an electrical rotation means which requires little maintenance.

According to an embodiment of the invention, the at least one rotation providing means comprises:

at least two rotary engines which are synchronized such that the first and second arms of the first and second cuff opening assemblies rotate synchronously around their respective geometrical axes.

An advantage with this embodiment is that a synchronized rotation of the first and second arms of the first and second cuff opening arrangements, respectively, can be achieved.

According to an embodiment of the invention, the garment fetching arrangement utilizes suction for fetching the garment from the garment storage and placing the garment in the donning position.

An advantage with this embodiment is that suction provides a simple, dependable, and proven way of attaching the garment to the fetching arrangement. Suction is further gentle on the garment.

According to an embodiment of the invention, the garment fetching arrangement comprises:

at least one end section; and a disc arranged inside the end section at a distance from an end of the end section; wherein the disc comprises one or more holes through which air can flow.

An advantage with this embodiment is that the risk that both sides of the garment is attached to the fetching arrangement is reduced.

Further applications and advantages of the present invention will be apparent from the following detailed description.

BRIEF DESCRIPTION OF THE DRAWINGS

The appended drawings are intended to clarify and explain different embodiments of the present invention, in which:

FIG. 3c shows a side view of a cuff opening assembly in an initial position according to an embodiment of the invention;

FIG. 3d shows a side view of a cuff opening assembly in an opening position according to an embodiment of the invention;

FIG. 3e shows details of an arm of a cuff opening assembly according to an embodiment of the invention;

DETAILED DESCRIPTION

Figure 1A:
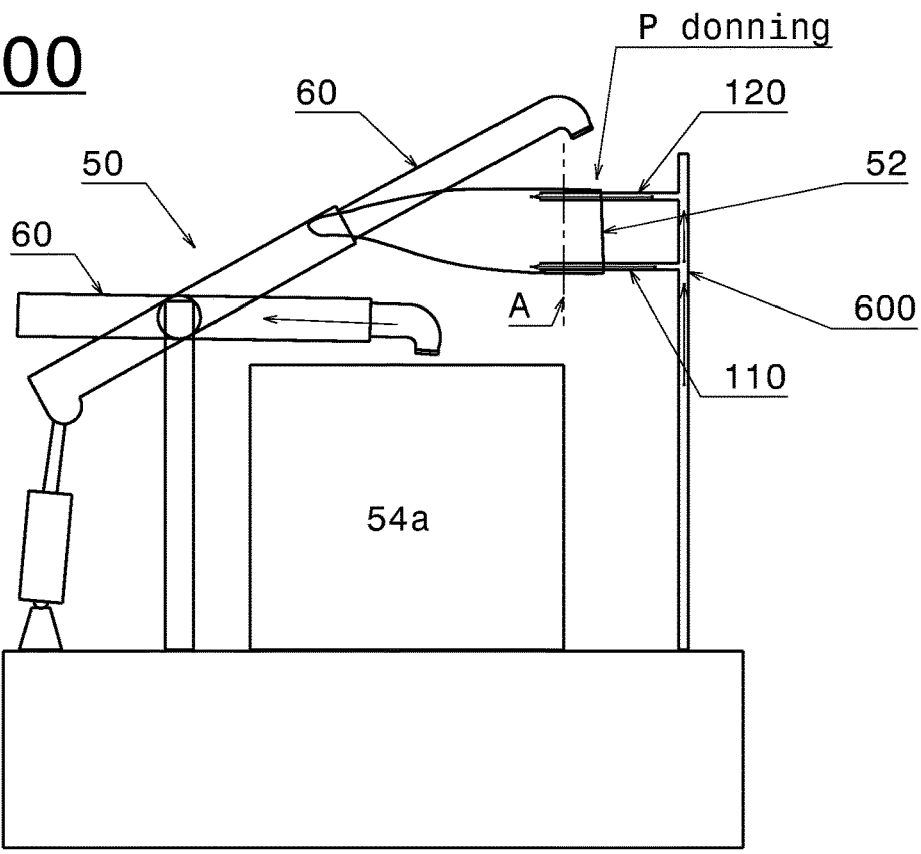
FIG. 1a shows a side view of a glove donning apparatus according to an embodiment of the invention.
Figure 1B:
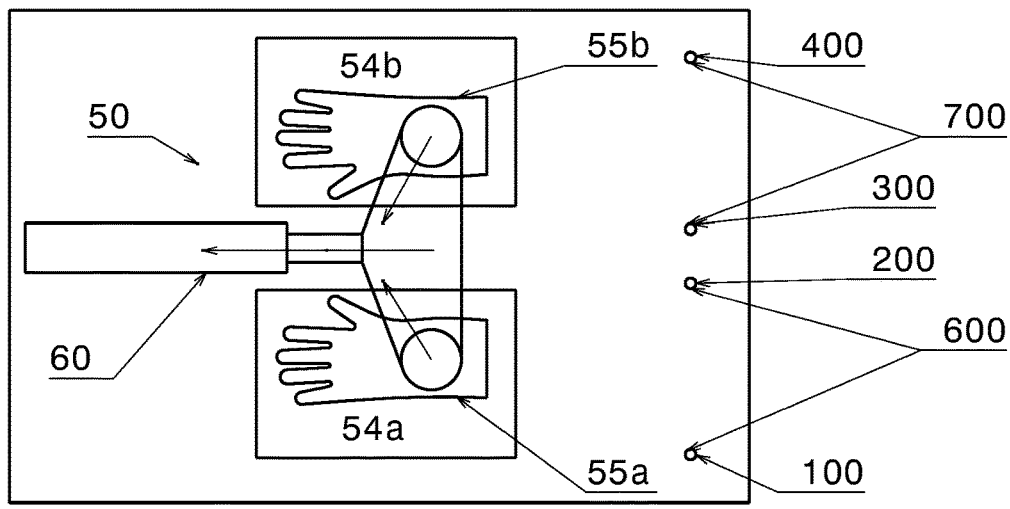
FIG. 1b shows a top view of a glove donning apparatus according to an embodiment of the invention.

FIG. 1a-b schematically illustrates an apparatus 800 according to various embodiments of the invention. FIG. 1a shows a side view of the apparatus 800, while FIG. 1b shows a top view of the apparatus 300. The apparatus 800 is arranged for facilitating donning a garment comprising a cuff on a part of a human body. In the embodiment shown in FIG. 1a-b, the garment is a glove 52 and the apparatus 800 is arranged for donning two such gloves 52, one on each hand of a user. However, other types of garments such as e.g. socks may in embodiments be used in, i.e. may be donned by, an apparatus 800 according to the invention. In such embodiments, the apparatus 800 may be arranged for facilitating donning the other type of garment, e.g. donning a sock on a foot of a user.

The apparatus 800 according to the invention may comprise a garment fetching arrangement 50 arranged to fetch a glove 52 from a garment storage 54 and place the glove 52 in a donning position $P_{donning}$. In the embodiment shown in FIG. 1a-b, the garment fetching arrangement 50 comprises a movable arm using suction to fetch the gloves 52. However, in other embodiments other types of fetching arrangement 50 may be used without deviating from the scope of the invention. The garment fetching arrangement 50 in FIG. 1a-b is arranged to fetch two gloves 52 at a time, one glove 52 from a first glove storage 54a and another glove 52 from a second glove storage 54b, shown in FIG. 1b. According to some embodiments, less or more than two glove storages 54a, 54b may be used. Each glove storage 54a, 54b may comprise a stack of gloves 52.

The apparatus 300 may further comprise at least one cuff opening arrangement 600, 700 arranged to open a cuff of a glove 52 in the donning position $P_{donning}$. Each cuff opening arrangement 600, 700 can open one glove at a time. Hence, with one cuff opening arrangement, one glove at a time can be applied to a hand of a user. If two cuff opening arrangements are used, a user can apply gloves onto both hands at the same time.

In the embodiment shown in FIG. 1a-b, the apparatus 800 comprises a first cuff opening arrangement 600 and a second cuff opening arrangement 700 (visible in FIG. 1b). Hence, the apparatus 800 can be used for donning two gloves 52 at a time. FIG. 1a shows a side view of the apparatus 800, where the first cuff opening arrangement 600, the first glove storage 54a, and one glove 52 positioned in its donning position $P_{donning}$ is visible. The cuff of the glove 52 shown FIG. 1a has been opened by the first cuff opening arrangement 600 and is ready to be donned onto the hand of the user. FIG. 1b shows a top view of the apparatus 800 illustrating the position of two gloves 52 at the top of a stack of gloves in the first 54a and second 54b glove storages, respectively.

In the embodiment shown FIG. 1a-b, the garment fetching arrangement 50 comprises an arm 60 which is extendable, and which may be displaced vertically by tilting it. Thus, the garment fetching arrangement 50 may move between different position of which two positions are shown in FIG. 1a-b. A fetching position in which the garment fetching arrangement 50 is arranged to fetch gloves 52 from the first 54a and second 54b glove storages and a release position in which the garment fetching arrangement 50 has placed the gloves 52 in their respective donning position $P_{donning}$ and subsequently released the gloves 52. The arm 60 of the garment fetching arrangement 50 comprises a first end section 55a and a second end section 55b through which air can be sucked in. To fetch gloves 52 from the first 54a and second 54b glove storages, the arm 60 is arranged to position the first 55a and second 55b end sections of the arm 60 above the first 54a and second 54b glove storages, respectively. The arm 60 is then lowered towards the first 54a and second 54b glove storages until it reaches the fetching position, i.e. until each one of the first 55a and second 55b end sections of the arm 60 are in contact with a glove 52 at the top of the stack of gloves in the first 54a and second. 54b glove storages, respectively. The arm 60 is then in the fetching position shown in FIG. 1a-b and can fetch two gloves 52, one from each glove storage 54a, 54b. The arm 60 may e.g. use suction to pick up the gloves 52, as indicated by the arrows in FIG. 1a-b, which represent a possible air flow through the arm 60. Further details related to embodiments where the garment fetching arrangement 50 uses suction to fetch a garment 52 will be described below with reference to FIGS. 7a-b. When the arm 60 has fetched the gloves 52, the arm 60 is moved up and forward to place the gloves 52 in their respective donning positions $P_{donning}$. The first 600 and second 700 cuff opening arrangements are arranged to be inserted into a cuff of a glove 52 and further open the cuff of the glove 52 in the donning positions $P_{donning}$. Once the first 600 and second 700 cuff opening arrangements are inserted into the cuffs of the gloves 52, the first 55a and second 55b end sections of the arm 60 are released from the gloves 52 by a reduction of the suction force, i.e. by a reduction of the air flow. The arm 60 is then lifted from the gloves to the release position shown in FIG. 1a. Before the donning of the glove 52, the arm 60 may be further removed from the gloves 52, e.g. back to the fetching position shown in FIGS. 1a-b or to another default position of the arm 60, to not be in the way during the donning. The first 600 and second 700 cuff opening arrangements open the cuffs of the gloves 52 to the extent that the user can easily insert his or her hands into the gloves 52. Thereby, donning one glove 52 on each hand of the user of the apparatus 800 is achieved.

Each cuff opening arrangement 600, 700 comprises a first and a second cuff opening assembly. FIG. 1b shows a first 100 and a second 200 cuff opening assembly of the first cuff opening arrangement 600, as well as a first 300 and a second 400 cuff opening assembly of the second cuff opening arrangement 700. Each of the first 100, 300 and second 200, 400 cuff opening assemblies comprises a first arm and a second arm of which only a first arm 110 and a second arm 120 of the first cuff opening assembly 100 of the first cuff opening arrangement 600 is visible in FIG. 1a. The first arms and second arms of each of the first 100, 300 and second 200, 400 cuff opening assemblies are arranged to be inserted into a cuff of a glove 52 and move apart such that the cuff of the glove 52 is expanded, making the cuff of the glove 52 bigger than it is in its relaxed state. As will now be described with reference to FIGS. 2a-2b.

Figure 2A:
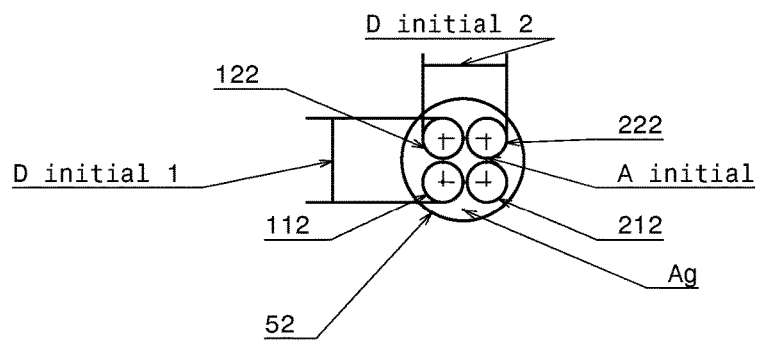
FIG. 2a show a cross section of a cuff opening arrangement in an initial position according to an embodiment of the invention.
Figure 2B:
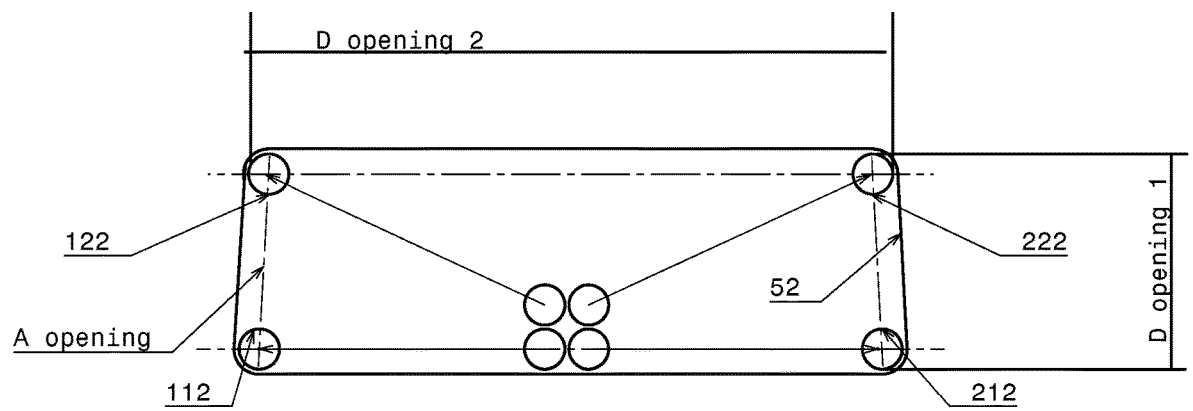
FIG. 2b show a cross section of a cuff opening arrangement in an opening position according to an embodiment of the invention.

FIGS. 2a-b shows a cross section along the line A in FIG. 1a of the apparatus 800 and illustrate the movement of the first 100 and second. 200 cuff opening assemblies from an initial position $P_{initial}$ to an opening position $P_{opening}$. During the movement, a first arm 110 and a second arm 120 of the first cuff opening assembly 100, and a first arm 210 and a second arm 220 of the second cuff opening assembly 200, all move relative to each other. The first arms 110, 210 of the first 100 and second 200 cuff opening assemblies, respectively, comprises a first proximal end 111, 211 and a first distal end 112, 212, and is rotatable around a first geometrical shaft axis GA1, as illustrated in FIGS. 3a-d and 4a-b. In a similar way, the second arm 120, 220 of the first 100 and second 200 cuff opening assemblies, respectively, comprises a second proximal end 121, 221 and a second distal end 122, 222, and is rotatable around a second geometrical axis GA2. As FIGS. 2a-b shows a cross section of a part of the apparatus 800, only the first 112, 212 and the second 122, 222 distal ends of the first 100 and second 200 cuff opening assemblies, respectively, are shown in these figures. The other parts of the first 100 and second 200 cuff opening assemblies are shown in FIGS. 3a-d and 4a-b, as mentioned above.

The first 110, 210 and second 120, 220 arms are arranged to rotate around the first GA1 and second GA2 geometrical axes, respectively, between the initial position $P_{initial}$ and the opening position $P_{opening}$. FIG. 2a shows the positions of the first 112, 212 and second 122, 222 distal ends relative to each other and relative to an opening of a glove 52 in the donning position $P_{donning}$, when the first 110, 210 and second 120, 220 arms are in the initial position $P_{initial}$. As shown in FIG. 2a, the first 112, 212 and second 122, 222 distal ends are at a first initial distance $D_{initial1}$ from each other in the initial position $P_{initial}$. In addition, the first 112 and the second 122 distal ends of the first 110 and second 120 arms of the first cuff opening assembly 100 are at a second initial distance $D_{initial2}$ from the first 212 and the second 222 distal ends of the first 210 and second 220 arms of the second cuff opening assembly 200, respectively, in the initial position $P_{initial}$. The first initial distance $D_{initial1}$ and the second initial distance $D_{initial2}$ are arranged to be small, e.g. close to zero, such that the first 112, 212 and second 122, 222 distal ends are close together in the initial position $P_{initial}$. Thereby, the first 112, 212 and second 122, 222 distal ends may easily be inserted into a cuff of a glove 52 in the donning position $P_{donning}$ when the cuff of the glove 52 is in a relaxed, i.e. not expanded/unexpanded state. This is illustrated in FIG. 2a, which also shows an initial area $A_{initial}$ and an area of an opening of the garment $A_g$ in its relaxed state. The initial area $A_{initial}$ is defined by the first 112 and second 122 distal ends of the first 110 and second 120 arms of the first cuff opening assembly 100 and the first 212 and second 222 distal ends of the first 210 and second 220 arms of the second cuff opening assembly 200, in the initial position $P_{initial}$. As shown in FIG. 2a, the initial area $A_{initial}$ is smaller than the area of the opening of the glove $A_g$ in its relaxed state.

When the first 110, 210 and second 120, 220 arms are rotated around the first GA1 and second GA2 geometrical axes, respectively, from the initial position $P_{initial}$ to wards the opening position $P_{opening}$, the first 112, 212 and second 122, 222 distal ends are separated from each other. The separation caused by the rotation takes place both horizontally and vertically, i.e. the first distal ends 112, 212 move away from the second distal ends 122, 222 of each one of the first 100 and second 200 cuff opening assembly, respectively, at the same time as the first 112 and second 122 distal ends of the first cuff opening assembly 100 move away from the first 212 and second 222 distal ends of the second cuff opening assembly 200, as indicated by the arrows in FIG. 2b. Furthermore, the first 112, 212 and second 122, 222 distal ends may be inserted into the cuff of the glove 52 placed in the donning position $P_{donning}$ when the first 110, 210 and second 120, 220 arms are rotated around the first GA1 and second GA2 geometrical axes, respectively, from the initial position $P_{initial}$ to the opening position $P_{opening}$. In this way, the first 112, 212 and second 122, 222 distal ends are separated from each other inside the glove 52 and starts to expand the cuff of the glove 52 during the rotation.

Further rotation of the first 110, 210 and second 120, 220 arms around the first GA1 and second GA2 geometrical axes, respectively, brings the first 110, 210 and second 120, 220 arms to the opening position $P_{opening}$. FIG. 2b shows the positions of the first 112, 212 and second 122, 222 distal ends relative to each other, when the first 110, 210 and second 120, 220 arms are in the opening position $P_{opening}$. As shown in FIG. 2b, the first 112, 212 and second 122, 222 distal ends of each one of the first 100 and second 200 cuff opening assembly, respectively, have been separated to a first opening distance $D_{opening1}$ from each other in the opening position $P_{opening}$. The first opening distance $D_{opening1}$ is arranged to be greater than the first initial distance $D_{initial1}$. In addition, the first 112 and second 122 distal ends of the first 110 and second 120 arms of the first cuff opening assembly 100 are at a second opening distance $D_{opening2}$ from the first 212 and second 222 distal ends of the first 210 and second 220 arms of the second cuff opening assembly 200, respectively, in the opening position $P_{opening}$. The second opening distance $D_{opening2}$ is arranged to be greater than the second initial distance $D_{initial2}$. Furthermore, the first opening distance $D_{opening1}$ and the second opening distance $D_{opening2}$ are arranged to be large enough to expand the cuff of the glove 52 in the donning position $P_{donning}$. In other worlds, the first 112 and second 222 distal ends of the first 110 and second 120 arms of the first cuff opening assembly 100 and the first 212 and second 222 distal ends of the first 210 and second 220 arms of the second cuff opening assembly 200 in the opening position $P_{opening}$ defines an opening area $A_{opening}$, where the opening area $A_{opening}$ is greater than the area of the opening of the glove Ag in its relaxed state, shown in FIG. 2a.

As described above and illustrated in FIGS. 2a-b, the first 112, 212 and second 122, 222 distal ends are separated from each other when the first 110, 210 and second 120, 220 arms are rotated around the first GA1 and second GA2 geometrical axes, respectively, from the initial position $P_{initial}$ towards the opening position $P_{opening}$. According to embodiments of the invention, the separation of the first 112, 212 and second 122, 222 distal ends during the rotation is achieved by arranging the first GA1 and second GA2 geometrical axes with an angle α to each other, i.e. the first GA1 and second GA2 geometrical axes have an angle α relative to each other. The angle α is selected to be different/other than 0 or 180 degrees, such that the first GA1 and second GA2 geometrical axes do not have the same orientation. Thus, the first GA1 and second GA2 geometrical axes are oblique, i.e. non-parallel, to each other. The orientation of the first geometrical axis GA1 thus differs from the orientation of the second geometrical axis GA2, such that the first GA1 and second GA2 geometrical axes intersect, as shown e.g. in FIGS. 2c-d.

Figure 2C:
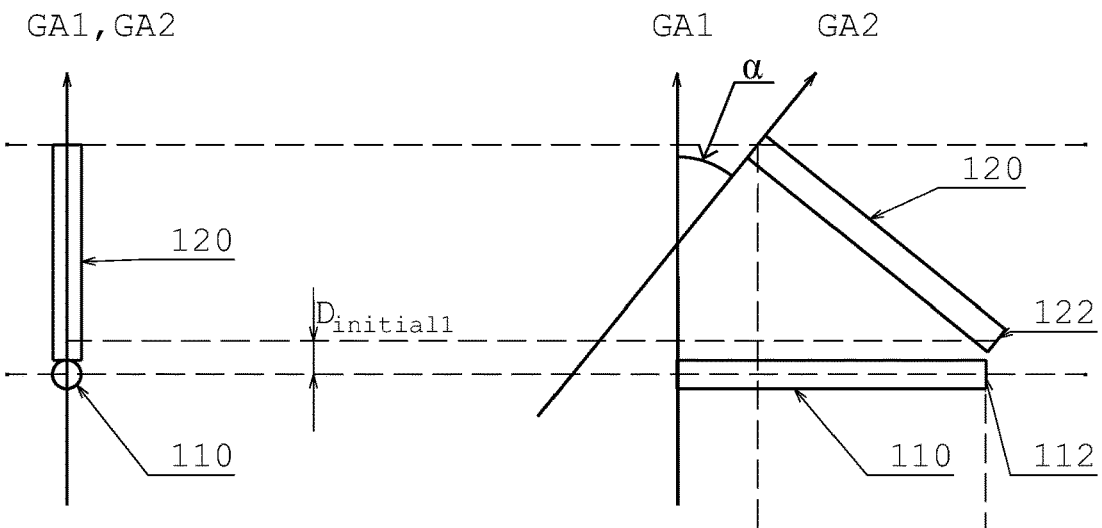
FIG. 2c show different views of a cuff opening assembly in an initial position according to an embodiment of the invention.
Figure 2D:
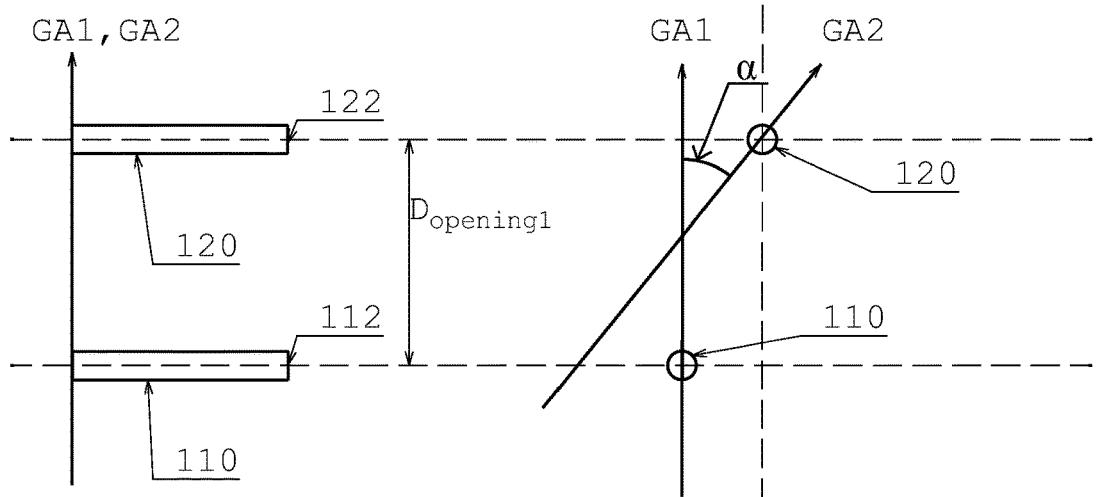
FIG. 2d show different views of a cuff opening assembly in an opening position according to an embodiment of the invention.

FIGS. 2c-d show embodiments for a first cuff opening assembly 100. In FIG. 2c, the first cuff opening assembly 100 is shown in the initial position $P_{initial}$, in two different side views and in a top view. In FIG. 2d, the first cuff opening assembly 100 is shown in the opening position $P_{opening}$, in two different side views and in a top view. In the embodiments shown in FIGS. 2c-d, the first GA1 and second GA2 geometrical axes are arranged with an angle α to each other. The angle α is selected such that the first 112 and second 122 distal ends of the first cuff opening assembly 100 are at the first initial distance $D_{initial1}$ from each other in the initial position $P_{initial}$, as shown in FIG. 2c. The angle α is further selected such that the first 112 and second 122 distal ends of the first cuff opening assembly 100 are separated to the first opening distance $D_{opening1}$ from each other in the opening position $P_{opening}$, as shown in FIG. 2d, when the first 110 and second 120 arms are rotated around the first GA1 and second GA2 geometrical axes, respectively. In the same way, the first GA1 and second GA2 geometrical axes around which the first 210 and second 220 arms of the second cuff opening assembly 200 rotates may be arranged to each other with an angle α, where the angle α is selected such that the first 212 and second 222 distal ends of the second cuff opening assembly 200 are at the first initial distance $D_{initial1}$ from each other in the initial position $P_{initial}$, and are separated to the first opening distance $D_{opening1}$ from each other in the opening position $P_{opening}$ (not shown in FIGS.).

Figure 3A:
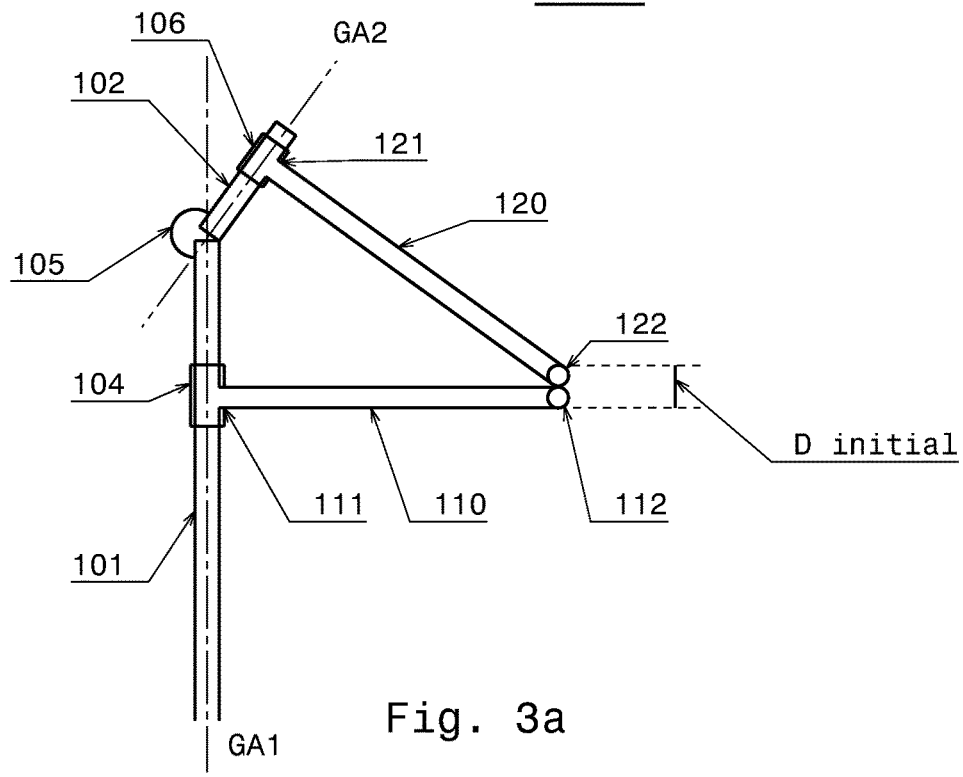
FIG. 3a shows a side view of a cuff opening assembly in an initial position according to an embodiment of the invention.
Figure 3B:
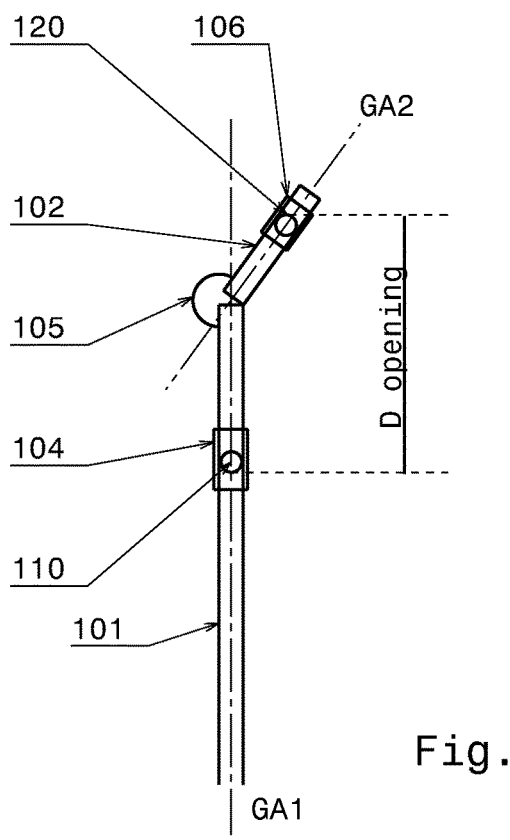
FIG. 3b shows a side view of a cuff opening assembly in an opening position according to an embodiment of the invention.

The rotation of the first 110, 210 and second 120, 220 arms around the first GA1 and second GA2 geometrical axes, respectively, may be achieved in different ways. FIGS. 3a and 3b shows an embodiment where the rotation of the first 110 and second 120 arms of the first cuff opening assembly 100 takes place around a first 101 and a second 102 shaft, respectively. The first shaft 101 extends along the first geometrical axis GA1, while the second shaft 102 extends along the geometrical axis GA2. Furthermore, the first 101 and second 102 shafts are fixed in relation to each other, and possibly also in relation to the apparatus 800. The first arm 110 is arranged to rotate around the first shaft 101 extending along the first geometrical axis GA1 and the second arm 120 is arranged to rotate around the second shaft 102 extending along the geometrical axis GA2. In the embodiment shown in FIGS. 3a and 3b, the first arm 110 is rotatably attached to the first shaft 101 with a first attachment means 104, and the second arm 120 is rotatably attached to the second shaft 102 with a second attachment means 106. The first 104 and second 106 attachment means may include e.g. a tubular sleeve or a similar arrangement.

In the embodiment shown in FIGS. 3b and 3c the rotation of the first 110 and second 120 arms of the first cuff opening assembly 100 is also based on a first 101 shaft extending along the first geometrical axis GA1 and a second shaft 102 extending along the geometrical axis GA2. However, in the embodiment shown in FIGS. 3b and 3c, the first 101 and second 102 shafts are instead arranged to rotate around their own axis, while maintaining the angle α relative to each other. Thus, in FIGS. 3c and 3d the first arm 110 is arranged to rotate together with the rotatable first shaft 101 extending along the first geometrical axis GA1 and being rotatable around the first geometrical axis GA1. Furthermore, the second arm 120 is arranged to rotate together with a rotatable second shaft 102 extending along the second geometrical axis GA2 and being rotatable around the second geometrical axis GA2. The first 101 and second 102 shafts may e.g. be attached to each other with a suitable coupling, which may include at least one gearwheel/cogwheel, e.g. a cardan/universal/gear joint. Although not shown in the figures, the rotation of the first 210 and second 220 arms of the second cuff opening assembly 200 may be achieved in the same way as for the embodiment shown in FIGS. 3a-b or as for the embodiment shown in FIGS. 3c-d for the first cuff opening assembly 100.

To allow the first 110, 210 and second 120, 220 arms of the first 100 and second 200 cuff opening assemblies to expand the glove 52 without getting caught in the glove 52 and without ripping the glove 52, the first 110, 210 and second 120, 220 arms may comprise parts which can move or rotate relative to the glove 52. According to some embodiments of the invention, the first 110, 210 and second 120, 220 arms may hence comprise an inner part and an outer part, where the outer part may be arranged to rotate around the inner part. In this way, the friction between the first 110, 210 and second 120, 220 arms and the glove 52 may be adjusted to match the properties of the glove 52, e.g. the friction may be reduced. FIG. 3e shows such an embodiment for the first arm 110 of the first cuff opening assembly 100. However, the principles shown in FIG. 3e may also be applied to the other arms. In FIG. 3e, the first arm 110 comprises an inner part 106 and an outer part 108. The outer part 108 is arranged to rotate around the inner part 106, e.g. by use of bearings. Hence, when the first arm 110 rotates from the initial position to the opening $P_{initial}$ position $P_{opening}$ inside the glove 52, the outer part 108 of the first arm 110 may rotate relative to the glove 52, thereby reducing the rotational friction between the first arm 110 and the glove 52.

To ensure that the glove 52 stays on the first 110, 210 and second 120, 220 arms during the expansion of the glove 52, the material of the outer part 108 may be selected such that a suitable longitudinal friction is achieved between the glove 52 and the first 110, 210 and second 120, 220 arms. Furthermore, the surface structure of the outer part 108 may be formed such that a suitable longitudinal friction is achieved between the glove 52 and the outer part 108. For example, the outer part 108 may comprise grooves or notches for engaging with the cuff of the glove 52. In this way, the risk of the glove 52 slipping of the first 110, 210 and second 120, 220 arms during the expansion of the glove 52 or when the hand is inserted into the glove 52 is reduced. In FIG. 3e, the grooves are illustrated as comprising four equally distanced v-shaped grooves arranged around the outer part 108. However, any number or shape of grooves may be used without deviating from the scope of the invention. Thus, the material and/or the surface structure of the outer part 108 may be selected such that a suitable longitudinal friction is achieved between the glove 52 and the outer part 108. In a similar way, the material and/or the surface structure of the first 110, 210 and second 120, 220 arms in embodiments where the first 110, 210 and second 120, 220 arms do not comprise an outer part 108 may also be selected such that a suitable longitudinal friction is achieved between the glove 52 and the outer part 108.

According to some embodiments of the invention, air may be blown into the glove 52 when it has been expanded, to further facilitate the donning of the glove 52. The air may e.g. be provided from an air supply through a nozzle which may be external or integrated into the first 100 and second 200 cuff opening assemblies. According to some embodiments the air may e.g. be supplied through the first 110, 210 and second 120, 220 arms of the first 100 and second 200 cuff opening assemblies. FIG. 3e shows such an embodiment for the first arm 110 of the first 100 cuff opening assembly. However, the same principles apply to any one of the arms 110, 120, 210, 220. In the embodiment shown in FIG. 3e, the first arm 110 is hollow and air may be blown through the first arm 110 and out through the first distal end 112. In this way, the first arm 110 may e.g. blow air into the glove 52 in the expanded state, thereby inflating the glove 52 such that the donning of the glove 52 is facilitated.

Alternative ways of implementing the separation of the first 112, 212 and second 122, 222 distal ends when the first 110, 210 and second 120, 220 arms are rotated around the first GA1 and second GA2 geometrical axes, respectively, may e.g. be based on a groove in the first 101, 201 and/or second 102, 202 shafts or a thread arranged to guide the rotation of the first 110, 210 and second 120, 220 arms. In embodiments based on a groove, the first 101, 201 and second 102, 202 shafts may be aligned, and the groove may be fixed in relation to at least one of the first 101, 201 and second 102, 202 shafts. At least one of the first 110, 210 and second 120, 220 arms is then guided by the groove in its rotation, such that the first 112, 212 and second 122, 222 distal ends are at the first initial distance $D_{init1}$ from each other in the initial position $P_{initial}$, and are separated to the first opening distance $D_{opening1}$ from each other in the opening position $P_{opening}$, when the first 110, 210 and second 120, 220 arms are rotated around the first 101, 201 and second 102, 202 shafts, respectively. In embodiments based on a thread, the first 101, 201 and second 102, 202 shafts may be aligned and at least one of the first 101, 201 and second 102, 202 shafts may comprise a thread. At least one of the first 110, 210 and second 120, 220 arms is guided by the thread in its rotation, such that the first 112, 212 and second 122, 222 distal ends are at the first initial distance $D_{init1}$ from each other in the initial position $P_{initial}$, and are separated to the first opening distance $D_{opening1}$ from each other in the opening position $P_{opening}$, when the first 110, 210 and second 120, 220 arms are rotated around the first 101, 201 and second 102, 202 shafts, respectively.

According to some embodiments of the invention, each of the first arms 110, 210 and the second arms 120, 220 of the first 100 and second 200 cuff opening assemblies, respectively, comprise two parts resiliently connected and arranged at an angle to each other. In this way, the insertion of the first arms 110, 210 and the second arms 120, 220 of the first 100 and second 200 cuff opening assemblies, respectively, into the cuff of the glove 52 may be simplified. In such embodiments, the first arm 110, 210 comprises a first proximal part 113, 213 and a first distal part 114, 214 resiliently connected to each other. Furthermore, the second arm 120, 220 comprises a second proximal part 123, 223 and a second distal part 124, 224 resiliently connected to each other. The first 113, 213 and the second 123, 223 proximal parts may e.g. be resiliently connected to the first 114, 214 and the second 124, 224 distal parts, respectively, by means of at least one spring joint or a resilient material of the first 110, 210 and second 120, 220 arms.

Figure 4A:
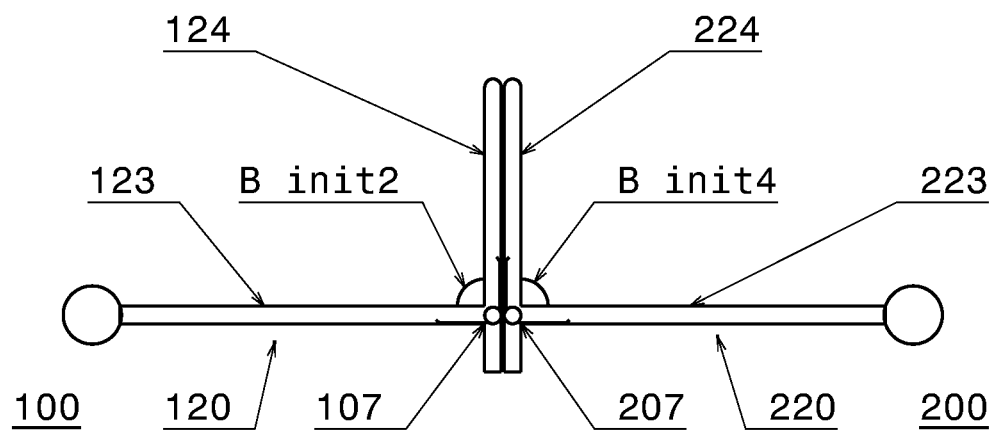
FIG. 4a shows a top view of cuff opening assemblies in an initial position according to an embodiment of the invention.
Figure 4B:
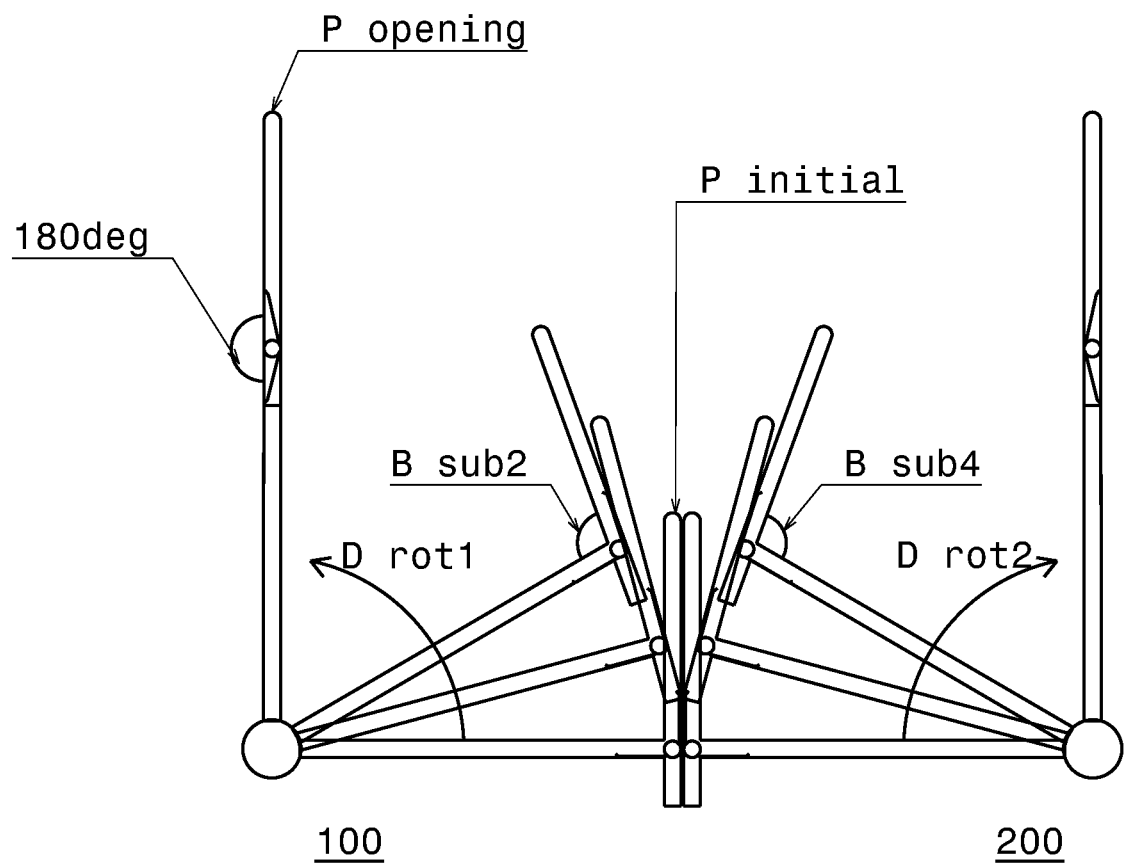
FIG. 4b shows a top view of cuff opening assemblies in initial and different subsequent positions according to an embodiment of the invention.

FIGS. 4a-b show a top view of a first 100 and a second 200 cuff opening assembly where the first 110, 210 and second 120, 220 arms of the first 100 and second 200 cuff opening assemblies, respectively, comprise two resiliently connected parts. As FIGS. 4a-b shows a top view only the second arms 120, 220 of the first 100 and second 200 cuff opening assemblies, respectively, are visible. The second arm 120 of the first cuff opening assembly 100 comprises a second proximal part 123 and a second distal part 124 resiliently connected with a spring joint 107. Furthermore, the second arm 220 of the second cuff opening assembly 200 comprises a second proximal part 223 and a second distal part 224 resiliently connected with a spring joint 207. Although not shown in FIGS. 4 a-b, the first 110, 210 arms of the first 100 and second 200 cuff opening assemblies are in a similar way comprising a first proximal part 113, 213 and a first distal part 114, 214 resiliently connected to each other, e.g. with spring joints.

In FIG. 4a the second arms 120, 220 of the first 100 and second 200 cuff opening assemblies, respectively, are shown in the initial position $P_{initial}$. In the initial position $P_{initial}$, the first 114 and second 124 distal parts of the first cuff opening assembly 100 may be in contact with the first 214 and second 224 distal parts of the second cuff opening assembly 200, respectively. Thereby, the first distal part 114 of the first cuff opening assembly 100 are at a first initial angle to the first proximal part 113 of the first cuff opening assembly 100, and the first distal part 214 of the second cuff opening assembly 200 are at a third initial angle $\beta_{init3}$ to the first proximal part 213 of the second cuff opening assembly 200 (not shown in the FIGS.). Furthermore, the second distal part 124 of the first cuff opening assembly 100 are at a second initial angle $\beta_{init2}$ to the second proximal part 123 of the first cuff opening assembly 100, and the second distal part 224 of the second cuff opening assembly 200 are at a fourth initial angle $\beta_{init4}$ to the second proximal part 223 of the second cuff opening assembly 200, as shown in FIG. 4a.

In the embodiment shown in FIG. 4a, the length of the second distal parts 124, 224 and the second proximal part 123, 223 are selected such that the second distal part 124 of the first cuff opening assembly 100 and the second distal part 224 of the second cuff opening assembly 200 are parallel to each other and in contact with each other in the initial position $P_{initial}$. Thereby, the second initial angle $\beta_{init2}$ and the fourth initial angle $\beta_{init4}$ is approximately 90 degrees in the initial position $P_{initial}$, as shown in FIG. 4a. In a similar way, the length of the first distal parts 114, 214 and the first proximal part 113, 213 are selected such that the first distal part 114 of the first cuff opening assembly 100 and the first distal part 214 of the second cuff opening assembly 200 are parallel to each other and in contact with each other in the initial position $P_{initial}$. Thereby, the first initial angle $\beta_{init1}$ and the third initial angle $\beta_{init3}$ is approximately 90 degrees in the initial position $P_{initial}$ (not shown in FIGS.).

When the first 110, 210 and second 120, 220 arms rotate around the first GA1 and second GA2 geometrical axes, respectively, the first 114 and second 124 distal parts of the first cuff opening assembly 100 will move away from the first 214 and second 224 distal parts of the second cuff opening assembly 200, leaving room for each distal part to move relative to the proximal part it is connected to. Due to the resilient connection between each distal and proximal part, the rotation may hence lead to that the angle β between the distal parts and the proximal parts changes, typically increases. Furthermore, as the first 110, 210 and second 120, 220 arms rotate, the first 114, 214 and second 124, 224 distal parts of the first 100 and second 200 cuff opening assemblies meet an inside of the cuff of the glove 52 and starts to expand the cuff of the glove 52. The resistance from the glove 52 leads to a force on the first 114, 214 and second 124, 224 distal parts of the first 100 and second 200 cuff opening assemblies, which will further increase the angle β between the distal parts and the proximal parts.

FIG. 4b shows the second arms 120, 220 of the first 100 and second 200 cuff opening assemblies, respectively, in different subsequent position as the second arms 120, 220 of the first 100 and second 200 cuff opening assemblies rotate away from the initial position $P_{initial}$ towards the opening position $P_{opening}$. As shown in FIG. 4b, the angle β between the second distal part 124 and the second proximal part 123 of the first cuff opening assembly 100 increases when the second arm 120 of the first cuff opening assembly 100 rotates away from the initial position $P_{initial}$. In a similar way, the angle β between the second distal part 224 and the second proximal part 223 of the second cuff opening assembly 200 increases when the second arm 220 of the second cuff opening assembly 200 rotates away from the initial position $P_{initial}$. The angle β between the second distal part 124 and the second proximal part 123 of the second arm 120 of the first cuff opening assembly 100 in a subsequent position is herein denoted a second subsequent angle $\beta_{sub2}$, and the angle β between the second distal part 224 and the second proximal part 223 of the second arm 220 of the second cuff opening assembly 200 in a subsequent position is herein denoted a fourth subsequent angle $\beta_{sub4}$, as shown in FIG. 4b. Corresponding subsequent angles for the first arms 110, 210 of the first 100 and second 200 cuff opening assemblies are denoted a first subsequent angle $\beta_{sub1}$ and a third subsequent angle respectively.

When the second arms 120, 220 of the first 100 and second 200 cuff opening assemblies, respectively, have reached the opening position $P_{opening}$, the second subsequent angle $\beta_{sub2}$ and the fourth subsequent angle $\beta_{sub4}$ may be approximately 180 degrees, as shown in FIG. 4b.

FIG. 4b shows the subsequent position for the second arms 120, 220 of the first 100 and second 200 cuff opening assemblies as they rotate towards the opening position $P_{opening}$. However, also the first arms 110, 210 of the first 100 and second 200 cuff opening assemblies behaves in a similar way. Consequently, in a subsequent position, the first 114, 214 and second 124, 224 distal parts of the first 100 and second 200 cuff opening assemblies are in contact with an inside of the cuff of the glove 52, such that the first distal part 114 of the first cuff opening assembly 100 is at a first subsequent angle $\beta_{sub1}$ to the first proximal part 113 of the first cuff opening assembly 100, the second distal part 124 of the first cuff opening assembly 100 is at a second subsequent angle $\beta_{sub2}$ to the second proximal part 123 of the first cuff opening assembly 100, the first distal part 214 of the second cuff opening assembly 200 are at a third subsequent angle $\beta_{sub3}$ to the first proximal part 213 of the second cuff opening assembly 200, and the second distal part 224 of the second cuff opening assembly 200 are at a fourth subsequent angle $\beta_{sub4}$ to the second proximal part 223 of the second cuff opening assembly 200.

The first subsequent angle $\beta_{sub1}$ is greater than the first initial angle the second subsequent angle $\beta_{sub2}$ is greater than the second initial angle $\beta_{init2}$, the third subsequent angle $\beta_{sub3}$ is greater than the third initial angle $\beta_{init3}$, and the fourth subsequent angle $\beta_{sub4}$ is greater than the fourth initial angle $\beta_{init4}$. Furthermore, when the subsequent position corresponds to the opening position $P_{opening}$, the first subsequent angle $\beta_{sub1}$, the second subsequent angle $\beta_{sub2}$, the third subsequent angle $\beta_{sub3}$, and the fourth subsequent angle $\beta_{sub4}$ are approximately 180 degrees.

Figure 4C:
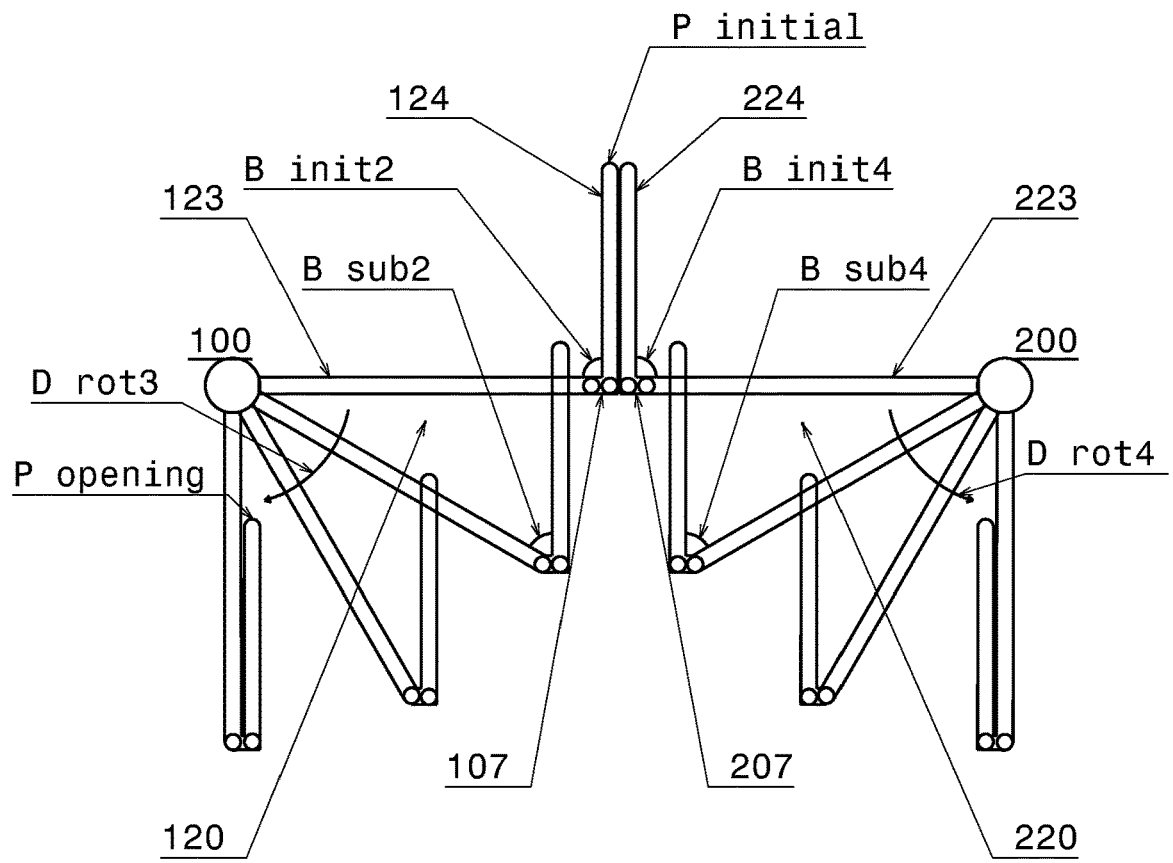
FIG. 4c shows a top view of cuff opening assemblies in initial and different subsequent positions according to an embodiment of the invention.
Figure 4D:
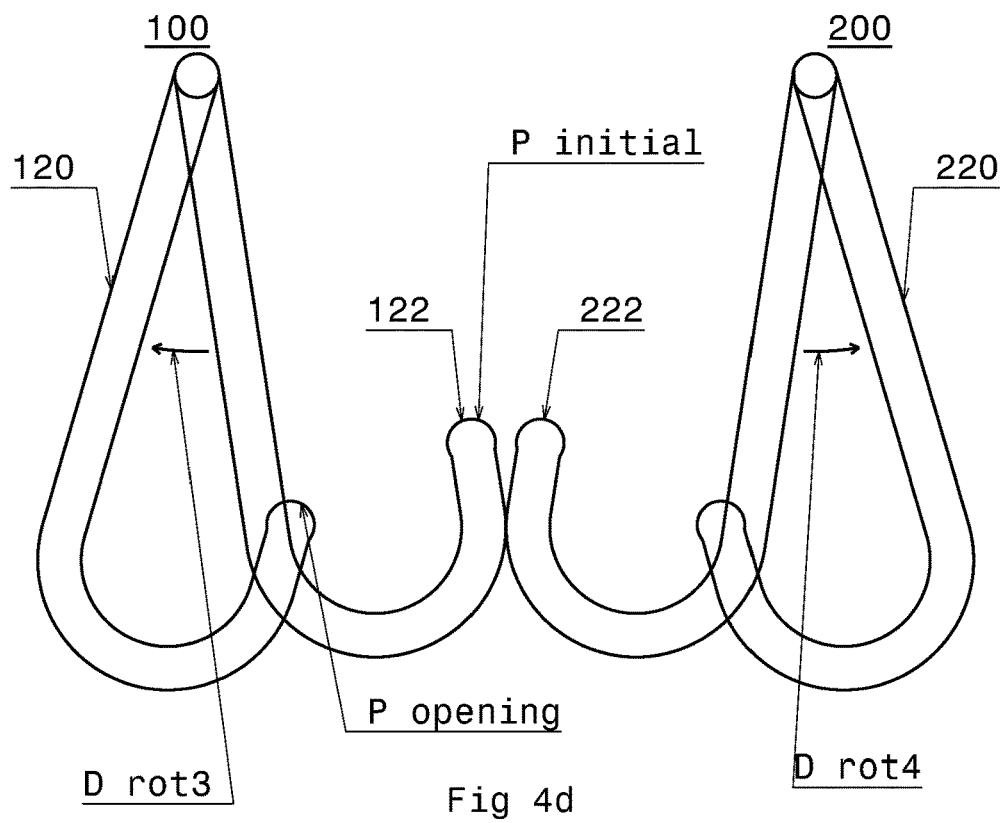
FIG. 4d shows a top view of cuff opening assemblies in initial and different subsequent positions according to an embodiment of the invention.

In the embodiment shown in FIG. 4b, the first 110 and second 120 arms of the first cuff opening assembly 100 rotates in a first rotation direction $D_{rot1}$, and the first 210 and second 220 arms of the second cuff opening assembly 200 rotates in a second rotation direction $D_{rot2}$, when moving from the initial position $P_{initial}$ to the opening position $P_{opening}$. As shown in FIG. 4b, the second rotation direction $D_{rot2}$ is opposite to the first rotation direction $D_{rot1}$. However, according to various embodiments, the first 110, 210 and second 120, 220 arms of the first 100 and second 200 cuff opening assemblies may instead rotate in opposite directions to the first $D_{rot1}$ and the second $D_{rot2}$ rotation direction, respectively. FIGS. 4c-d show examples of such embodiments.

As shown in FIG. 4c, the first 110 and second 120 arms of the first cuff opening assembly 100 rotates in a third rotation direction $D_{rot3}$, while the first 210 and second 220 arms of the second cuff opening assembly 200 rotates in a fourth rotation direction $D_{rot4}$. The fourth rotation direction $D_{rot4}$ is opposite to the third rotation direction $D_{rot3}$. In the embodiment shown in FIG. 4c, the first 114, 214 and second 124, 224 distal parts of the first 100 and second 200 cuff opening assemblies are linked to the first 113, 213 and second 123, 223 proximal parts of the first 100 and second 200 cuff opening assemblies, respectively, such that the first 114, 214 and second 124, 224 distal parts of the first 100 and second 200 cuff opening assemblies maintains their direction relative to the glove 52, when the first 110, 210 and second 120, 220 arms of the first 100 and second 200 cuff opening assemblies rotates to open the glove 52.

The linkage between the first 114, 214 and second 124, 224 distal parts of the first 100 and second 200 cuff opening assemblies and the first 113, 213 and second 123, 223 proximal parts of the first 100 and second 200 cuff opening assemblies can e.g. comprise a chain or other known means. Due to the linkage, the first subsequent angle $\beta_{sub1}$, the second subsequent angle $\beta_{sub2}$, the third subsequent angle $\beta_{sub3}$, and the fourth subsequent angle $\beta_{sub4}$ decreases as the first 110, 210 and second 120, 220 arms of the first 100 and second 200 cuff opening assemblies rotates towards the opening position $P_{opening}$, as shown in FIG. 4c for the second subsequent angle $\beta_{sub2}$ and the fourth subsequent angle $\beta_{sub4}$. When the first 110, 210 and second 120, 220 arms of the first 100 and second 200 cuff opening assemblies reaches the opening position $P_{opening}$, the first subsequent angle $\beta_{sub1}$, the second subsequent angle $\beta_{sub2}$, the third subsequent angle $\beta_{sub3}$, and the fourth subsequent angle $\beta_{sub4}$ may be approximately 0 degrees.

FIG. 4d shows a further embodiment where the first 110 and second 120 arms of the first cuff opening assembly 100 rotates in a third rotation direction $D_{rot3}$ and the first 210 and second 220 arms of the second cuff opening assembly 200 rotates in a fourth rotation direction $D_{rot4}$, when moving from the initial position $P_{initial}$ to the opening position $P_{opening}$. In the embodiment shown in FIG. 4d, the first 110, 210 and second 120, 220 arms of the first 100 and second 200 cuff opening assemblies are curve shaped, i.e. are shaped as hooks, and are curved/arched/bent such that the distal ends 112, 212, 122, 222 can easily be inserted into the cuff of a glove 52 placed in the donning position $P_{donning}$. When the first 110, 210 and second 120, 220 arms of the first 100 and second 200 cuff opening assemblies rotates from the initial position $P_{initial}$ towards the opening position $P_{opening}$, the distal ends 112, 122, 122, 222 of the first 100 and second 200 cuff opening assemblies are separated from each other such that the glove 52 is opened.

As FIG. 4d shows a top view only the second arms 120, 220 of the first 100 and second 200 cuff opening assemblies, respectively, are visible. Thus, FIG. 4d shows how the second distal end 122 of the second arm 120 of the first cuff opening assembly 100 is separated from the second distal end 222 of the second arm 220 of the second cuff opening assembly 200, when the second arm 120 of the first cuff opening assembly 100 rotates in the third rotation direction $D_{rot3}$ and the second arm 220 of the second cuff opening assembly 200 in the fourth rotation direction $D_{rot4}$. The length and the shape of the first 110, 210 and second 120, 220 arms of the first 100 and second 200 cuff opening assemblies are selected such that when the first 110, 210 and second 120, 220 arms of the first 100 and second 200 cuff opening assemblies reaches the opening position $P_{opening}$ the gloves 52 is opened to the extent that the user can easily insert his or her hands into the glove 52.

FIGS. 4a-d show a top view of the first 100 and second 200 cuff opening assemblies, therefore the first arms 110, 210 of the first 100 and second 200 cuff opening assemblies are not shown in these figures. However, as is understood by a skilled person, the first arms 110, 210 of the first 100 and second 200 cuff opening assemblies, respectively, are also rotated in a corresponding way as illustrated for the second arms 120, 220 in FIGS. 4a-d, and described above.

The first 110, 210 and second 120, 220 arms of the first 100 and second 200 cuff opening assemblies, respectively, may be coupled with a first coupling means such that the first 110, 210 and second 120, 220 arms rotates synchronously around the first GA1 and second GA2 geometrical axes, respectively. In other worlds, the first 110 and second 120 arms of the first cuff opening assembly 100 may be coupled such that the first 110 and second 120 arms rotate together, i.e. at the same time and in the same rotation direction, around or together with the first 101 and second 102 shafts, respectively. The first subsequent angle $\beta_{sub1}$ is in this case typically essentially equal to the second subsequent angle $\beta_{sub2}$. Furthermore, the first 210 and second 220 arms of the second cuff opening assembly may be coupled such that the first 210 and second 220 arms rotates together, i.e. at the same time and in the same rotation direction, around or together with the first 201 and second 202 shafts, respectively. The third subsequent angle $\beta_{sub3}$ is in this case typically essentially equal to the fourth subsequent angle $\beta_{sub4}$.

In addition, at least one of the first 110 and second 120 arms of the first cuff opening assembly 100 may be coupled to at least one of the first 210 and second 220 arms of the second cuff opening assembly 200 with a second coupling means, such that the first 110, 210 and second 120, 220 arms of the first 100 and second 200 cuff opening assemblies rotate synchronously around their respective geometrical axes GA2, GA2. In this case, the first subsequent angle $\beta_{sub1}$, the second subsequent angle $\beta_{sub2}$, the third subsequent angle $\beta_{sub3}$, and the fourth subsequent angle $\beta_{sub4}$ are typically essentially equal. Moreover, as described with reference to FIG. 4b, the first 110 and second 120 arms of the first cuff opening assembly 100 may rotate in the first rotation direction $D_{rot1}$, and the first 210 and second 220 arms of the second cuff opening assembly 200 may rotate in the second rotation direction $D_{rot2}$, where the second rotation direction $D_{rot2}$ is opposite to the first rotation direction $D_{rot1}$.

The rotation of the first 110, 210 and second 120, 220 arms of the first 100 and second 200 cuff opening assemblies around the first GA1 and second GA2 geometrical axes may be provided in several different ways. According to some embodiments of the invention at least one cuff opening arrangement 600, 700 further comprises at least one rotation providing means coupled to at least one of the first 110, 210 and second 120, 220 arms of the first 100 and second 200 cuff opening assemblies. The rotation providing means may be arranged to cause the rotation of at least one of the first 110, 210 and second 120, 220 arms of the first 100 and second 200 cuff opening assemblies between the initial position $P_{initial}$ and the opening position $P_{opening}$.

According to embodiments of the invention the rotation providing means may comprises at least one rod 510, 520 coupled to at least one of the first 110, 210 and second 120, 220 arms of the first 100 and second 200 cuff opening assemblies. When the at least one rod 510, 520 is in a first position the first 110, 210 and second 120, 220 arms of the first 100 and second 200 cuff opening assemblies are in the initial position $P_{initial}$. Furthermore, when the at least one rod 510, 520 is in a second position, the first 110, 210 and second 120, 220 arms of the first 100 and second 200 cuff opening assemblies are in the opening position $P_{opening}$. The displacement of the at least one rod 510, 520 may be provided with a displacement means 540. Hence, the at least one rotation providing means may comprise at least one displacement means 540 coupled to the at least one rod 510, 520 and arranged to displace the at least one rod 510, 520 between the first and second positions.

Figure 5:
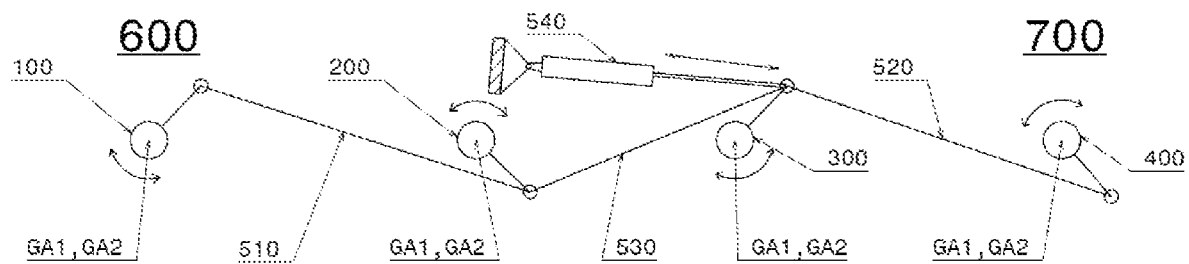
FIG. 5 shows coupling means and a rotation providing means according to an embodiment of the invention.

Furthermore, the at least one rod 510 of the first cuff opening arrangement 600 may be coupled to the at least one rod 520 of the second cuff opening arrangement 700. In this case, the rotation providing means may comprise a displacement means 540 coupled to one or more of the at least one rod 510, 520 of the first 600 or second 700 cuff opening arrangements, and arranged to displace the at least one rod 510, 520 of the first 600 and second 700 cuff opening arrangements, respectively, between the first and second positions FIG. 5 shows a rotation providing means according to an embodiment of the invention. In FIG. 5, a first 600 and a second 700 cuff opening arrangement is shown. A rod 510 is coupled to a first 100 and a second 200 cuff opening assembly of the first cuff opening arrangement 600, and a rod 520 is coupled to a third 300 and a fourth 400 cuff opening assembly of the second cuff opening arrangement 700. Furthermore, the rod 510 of the first cuff opening arrangement 600 is coupled to the rod 520 of the second cuff opening arrangement 700 with a coupling rod 530. The rotation providing means comprises a displacement means 540 attached to the coupling rod 530 and the rod 520 of the second cuff opening arrangement 700. The displacement means 540 is arranged to displace the rods 510, 520 of the first 600 and second 700 cuff opening arrangements, respectively, between the first and second positions. In the embodiment shown in FIG. 5, the displacement means 540 is a piston coupled to the rods 510, 520, 530 which displaces the rods 510, 520 of the first 600 and second 700 cuff opening arrangements by extracting and retracting the piston. However, the displacement means 540 may instead be another type of known displacement means.

According to embodiments of the invention the rotation of the first 110, 210 and second 120, 220 arms of the first 100 and second 200 cuff opening assemblies around the first GA1 and second GA2 geometrical axes may alternatively be provided using rotary engines. Hence, in some embodiments the at least one rotation providing means may comprise at least one rotary engine 551, 552 coupled to at least one of the first 110, 210 and second 120, 220 arms of the first 100 and second 200 cuff opening assemblies. The at least one rotary engine 551, 552 may be arranged to rotate the first 110, 210 and second 120, 220 arms of the first 100 and second 200 cuff opening assemblies from the initial position $P_{initial}$ to the opening position $P_{opening}$. If more than one rotary engine 551, 552 is used, the rotary engines 551, 552 may further be synchronized such that the first 110, 210 and second 120, 220 arms of the first 100 and second 200 cuff opening assemblies rotate synchronously around their respective geometrical axes GA1, GA2.

Figure 6:
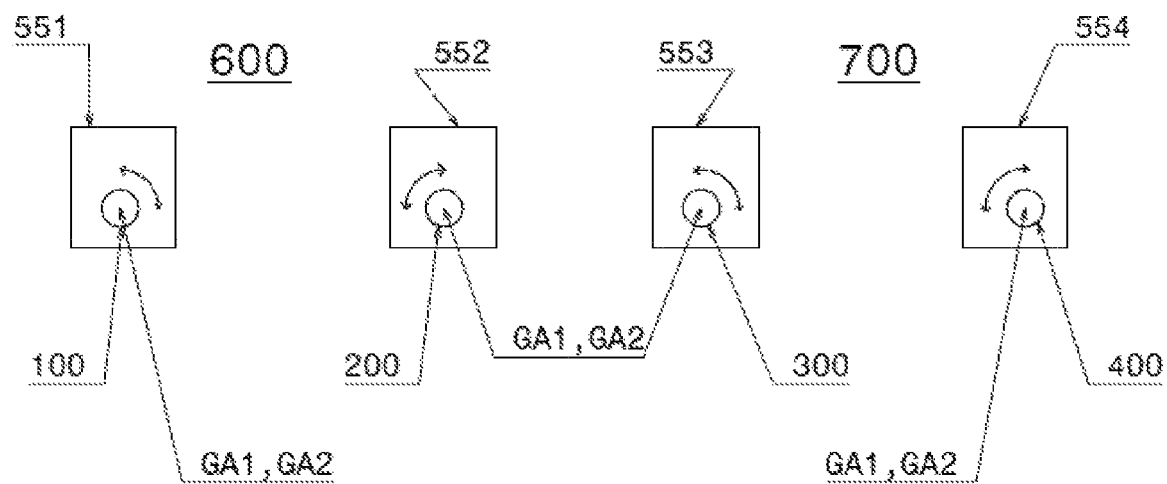
FIG. 6 shows rotation providing means according to an embodiment of the invention.

FIG. 6 shows an embodiment of the invention where the rotation providing means comprises at least one rotary engine. As in FIG. 5, FIG. 6 shows a first 600 and a second 700 cuff opening arrangement, where the first cuff opening arrangement 600 comprises a first 100 and a second 200 cuff opening assembly, and the second cuff opening arrangement 700 comprises a third 300 and a fourth 400 cuff opening assembly. In the embodiment shown in FIG. 6, the rotation of the first 100, second 200, third 300, and fourth 400 cuff opening assemblies are provided with a first 551, a second 552, a third 552, and a fourth 554 rotary engine. Each rotary engine 551, 552, 553, 554 is coupled to at least one of the first 110, 210 and second 120, 220 arms of one cuff opening assembly 100, 200, 300, 400, as shown in FIG. 6. The rotary engines 551, 552, 553, 554 are arranged to rotate the first 110, 210 and second 120, 220 arms of the first 100 and second 200 cuff opening assemblies, as well as the first 110, 210 and second 120, 220 arms of the third 300 and fourth 400 cuff opening assemblies, from the initial position $P_{initial}$ to the opening position $P_{opening}$. The rotary engines 551, 552, 553, 554 may further be synchronized such that the first 110, 210 and second 120, 220 arms of first 100, second 200, third 300, and fourth 400 cuff opening assemblies rotate synchronously around their respective geometrical axes GA1, GA2. According to embodiments of the invention, the rotary engines 551, 552, 553, 554 may e.g. be pneumatic engines or electrical engines.

It is to be noted that although some embodiments of the invention are herein described for a first 100 cuff opening assembly or a first 100 and a second 200 cuff opening assembly, e.g. the embodiments describe with reference to FIGS. 2a-4b, the same applies to each cuff opening assembly 100, 200, 300, 400 in each cuff opening arrangement 600, 700 of the apparatus 800.

Figure 7A:
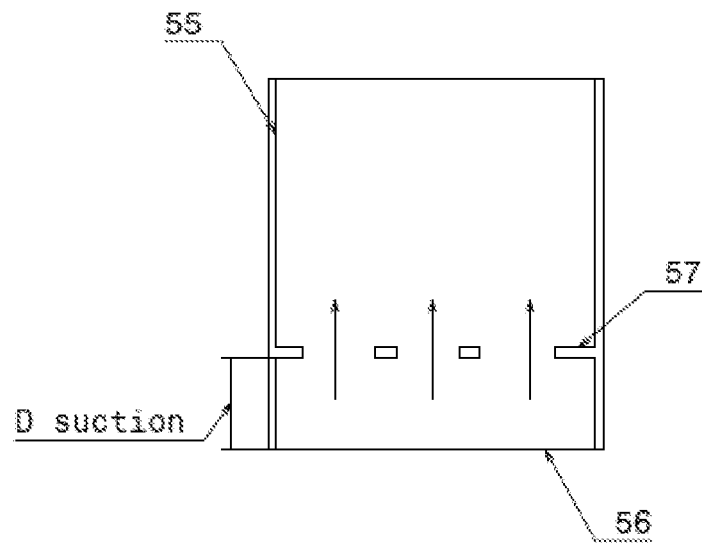
FIG. 7a shows a cross section of a garment fetching arrangement according to an embodiment of the invention.
Figure 7B:
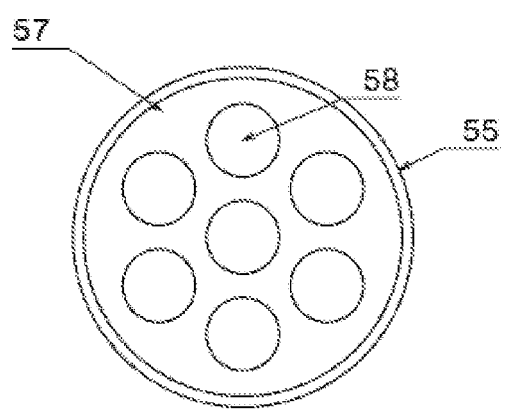
FIG. 7b shows a bottom view of a garment fetching arrangement according to an embodiment of the invention.

As previously described, the garment fetching arrangement 50 of the apparatus 800 may utilizes suction for fetching a glove 52 from a glove storage 54 and placing the glove 52 in a donning position $P_{donning}$. Further details related to a garment fetching arrangement 50 utilizing suction is described below with reference to FIGS. 7a-b. FIG. 7a shows a cross section of an end section 55 of a garment fetching arrangement 50 according to an embodiment of the invention. The FIG. 7b shows a bottom view of the end section 55 of the garment fetching arrangement 50. When the garment fetching arrangement 50 is arranged to fetch two gloves 52 at the same time, the garment fetching arrangement 50 may comprise two end sections 55. For example, a first 55a and a second 55b end section as shown in FIG. 1b. In this case, each end section 55a, 55b may be arranged as shown in FIGS. 7a-b.

The garment fetching arrangement 50 may be arranged to suck in air through the end section 55 such that when the end section 55 is positioned close to a glove 52 suction is created between the end section 55 and the glove 52. The glove 52 is thereby attached to the end section 55 and the garment fetching arrangement 50 can lift and move the glove 52 to the donning position $P_{donning}$. However, the garment fetching arrangement 50 should only attach to one side of the glove 52, leaving the other side of the glove 52 unattached, such that the glove 52 is opened when the garment fetching arrangement 50 lifts the glove 52 from the glove storage 54. In this way, the glove is open when being placed in the donning position $P_{donning}$, allowing the first 112, 212 and second 122, 222 distal ends to easily be inserted into the cuff of the glove 52, and thereafter open the glove 52, as previously described. According to an embodiment of the invention, to control the suction force such that only one side of the glove 52 is attached to the end section 55, the end section 55 includes a disc 57, which comprises one or more holes 58 through which air can flow, as shown in FIG. 7b. The disc 57 may be arranged inside the end section 55 at a distance $D_{suction}$ from an end 56 of the end section 55, as shown in FIG. 7a. Due to the distance $D_{suction}$ in combination with the air flowing through the holes 58, it is achieved that only the side of the glove 52 facing the end 56 of the end section 55 will be affected by the suction from the end section 55, leaving the other side of the glove 52 unattached, such that the glove 52 is opened. This is due to the fact that the two sides of the glove, i.e. the side facing the end 56 of the end section 55 and the side facing the garment storage 54, are moved relative to each other when the glove 52 is being sucked into the end sections 55 towards the disc 57. By this movement, the risk that the two sides of the glove 52 stick to each other, and therefore also the risk that the glove 52 does not open, is considerably reduced.

The invention claimed is:

1. An apparatus arranged for facilitating donning a garment comprising a cuff on a part of a human body, comprising:
    a garment fetching arrangement arranged for fetching a garment from a garment storage and placing said garment in a donning position;
    at least one cuff opening arrangement arranged to open a cuff of said garment in said donning position, and comprising a first and a second cuff opening assembly, each of said first and second cuff opening assemblies comprising:
    a first arm comprising a first proximal end and a first distal end, said first arm being rotatable around a first geometrical axis;
    a second arm comprising a second proximal end and a second distal end, said second arm being rotatable around a second geometrical axis; wherein
    said first and second arms are arranged to rotate around said first and second geometrical axes, respectively, between an initial position and an opening position, and said first and second geometrical axes are arranged with an angle a to each other, said angle a being selected such that said first and second distal ends are at a first initial distance from each other in said initial position, and are separated to a first opening distance from each other in said opening position, when said first and second arms are rotated around said first and second geometrical axes, respectively, said first opening distance being greater than said first initial distance.

2. An apparatus according to claim 1, wherein:
said first arm is arranged to rotate around a first shaft extending along said first geometrical axis; and
said second arm is arranged to rotate around a second shaft extending along said geometrical axis.

3. An apparatus according to claim 1, wherein:
said first arm is arranged to rotate together with a rotatable first shaft extending along said first geometrical axis and being rotatable around said first geometrical axis; and
said second arm is arranged to rotate together with a rotatable second shaft extending along said second geometrical axis and being rotatable around said second geometrical axis.

4. An apparatus according to claim 1, wherein said first and second distal ends are inserted into a cuff of a garment placed in said donning position when said first and second arms are rotated around said first and second geometrical axes, respectively, from said initial position to said opening position.

5. An apparatus according to claim 1, wherein
a first and a second distal ends of said first and second arms of said first cuff opening assembly are at a second initial distance $D_{initial2}$ from a first and a second distal ends of said first and second arms of said second cuff opening assembly, respectively, in said initial position;
said first and second distal ends of said first cuff opening assembly are at a second opening distance from said first and second distal ends of said second cuff opening assembly, respectively, in said opening position; and
said second opening distance is greater than said second initial distance.

6. An apparatus according to claim 1, wherein
said first and second distal ends of said first and second arms of said first cuff opening assembly and said first and second distal ends of said first and second arms of said second cuff opening assembly in said initial position defines an initial area; and
said initial area is smaller than an area of an opening of said garment in its relaxed state.

7. An apparatus according to claim 1, wherein
said first and second distal ends of said first and second arms of said first cuff opening assembly and said first and second distal ends of said first and second arms of said second cuff opening assembly in said opening position defines an opening area; and
said opening area is greater than an area of an opening of said garment in its relaxed state.

8. An apparatus according to claim 1, wherein
said first and second arms of said first and second cuff opening assemblies, respectively, are coupled with a first coupling means, such that said first and second arms rotate synchronously around said first and second geometrical axes, respectively.

9. An apparatus according to claim 8, wherein
at least one of said first and second arms of said first cuff opening assembly is coupled to at least one of said first and second arms of said second cuff opening assembly with a second coupling means, such that said first and second arms of said first and second cuff opening assemblies rotate synchronously around their respective geometrical axes; and
said first and second arms of said first cuff opening assembly rotate in a first rotation direction, and said first and second arms of said second cuff opening assembly rotate in a second rotation direction, said second rotation direction being opposite to said first rotation direction.

10. An apparatus according to claim 1, wherein said at least one cuff opening arrangement further comprises:
at least one rotation providing means coupled to at least one of said first and second arms of said first and second cuff opening assemblies, arranged to cause the rotation of at least one of said first and second arms of said first and second cuff opening assemblies between said initial position and said opening position.

11. An apparatus according to claim 10, wherein said at least one rotation providing means includes:
at least one rod coupled to at least one of said first and second arms of said first and second cuff opening assemblies; wherein
when said at least one rod is in a first position, said first and second arms of said first and second cuff opening assemblies are in said initial position; and
when said at least one rod is in a second position, said first and second arms of said first and second cuff opening assemblies are in said opening position.

12. An apparatus according to claim 11, wherein said at least one rotation providing means comprises:
at least one displacement means coupled to said at least one rod and arranged to displace said at least one rod between said first and second positions.

13. An apparatus according to claim 11, including:
a first cuff opening arrangement and a second cuff opening arrangement; wherein
at least one rod of said first cuff opening arrangement is coupled to at least one rod of said second cuff opening arrangement;
said at least one rotation providing means comprises:
a displacement means coupled to one or more of said at least one rod of said first or second cuff opening arrangements, and arranged to displace said at least one rod of said first and second cuff opening arrangements, respectively, between said first and second positions.

14. An apparatus according to claim 10, wherein said at least one rotation providing means comprises:
at least one rotary engine coupled to at least one of said first and second arms of said first and second cuff opening assemblies; wherein
said at least one rotary engine is arranged to rotate said first and second arms of said first and second cuff opening assemblies from said initial position to said opening position.

15. An apparatus according to claim 14, wherein said at least one rotation providing means comprises:
at least two rotary engines which are synchronized such that said first and second arms of said first and second cuff opening assemblies rotate synchronously around their respective geometrical axes.

* * * * *